(12) United States Patent
Pusch et al.

(10) Patent No.: US 8,679,036 B2
(45) Date of Patent: Mar. 25, 2014

(54) SYSTEM AND METHOD FOR VISUALIZING GROUND REACTION FORCES ON A HUMAN BODY

(75) Inventors: Martin Pusch, Duderstadt (DE); Sven Zarling, Duderstadt (DE); Sven Kaltenborn, Duderstadt (DE)

(73) Assignee: Otto Bock Healthcare GmbH, Duderstadt (DE)

( * ) Notice: Subject to any disclaimer, the term of this patent is extended or adjusted under 35 U.S.C. 154(b) by 585 days.

(21) Appl. No.: 12/299,930

(22) PCT Filed: Apr. 25, 2007

(86) PCT No.: PCT/DE2007/000737
§ 371 (c)(1),
(2), (4) Date: Nov. 7, 2008

(87) PCT Pub. No.: WO2007/128266
PCT Pub. Date: Nov. 15, 2007

(65) Prior Publication Data
US 2009/0118647 A1    May 7, 2009

(30) Foreign Application Priority Data
May 9, 2006    (DE) .................. 10 2006 021 788

(51) Int. Cl.
*A61B 5/103*    (2006.01)
*A61B 5/117*    (2006.01)

(52) U.S. Cl.
USPC .................... 600/587; 600/592; 600/595

(58) Field of Classification Search
USPC ........................ 600/587, 592, 595
See application file for complete search history.

(56) References Cited

U.S. PATENT DOCUMENTS

| | | | | |
|---|---|---|---|---|
| 4,598,717 | A * | 7/1986 | Pedotti ..................... | 600/592 |
| 4,779,629 | A * | 10/1988 | West et al. ................. | 600/587 |
| 4,819,660 | A * | 4/1989 | Smith ....................... | 600/587 |
| 5,609,162 | A * | 3/1997 | Blumentritt et al. ........ | 600/587 |
| 5,753,931 | A * | 5/1998 | Borchers et al. ........ | 250/559.22 |
| 6,387,061 | B1 * | 5/2002 | Nitto ......................... | 600/587 |
| 6,402,635 | B1 * | 6/2002 | Nesbit et al. ............... | 473/269 |

(Continued)

FOREIGN PATENT DOCUMENTS

| | | |
|---|---|---|
| DE | 10008059 | 5/2001 |
| DE | 102004046329 | 4/2006 |

(Continued)

OTHER PUBLICATIONS

International Search Report for PCT/DE2007/000737, mailed Jan. 22, 2008, 5 pgs.

*Primary Examiner* — Jeffrey G Hoekstra
*Assistant Examiner* — Devin Henson
(74) *Attorney, Agent, or Firm* — Holland & Hart

(57) ABSTRACT

The invention relates to a display system and method for measuring and displaying ground reaction forces of a human. The system comprising comprises a measurement plate having at least one sensor device for detecting ground reaction forces, which is connected to an evaluation device connected to the measurement plate and a projection device, and the invention also relates to a method for displaying ground reaction forces on a human body. The display system and the method are suitable in particular for measuring the human body and/or prosthetic or orthotic fit components in their relative position to the human body, and for improving the adjustment of a prosthesis set up.

7 Claims, 3 Drawing Sheets

(56) References Cited

U.S. PATENT DOCUMENTS

| | | | |
|---|---|---|---|
| 6,684,165 B2 * | 1/2004 | Peisner | 702/41 |
| 7,447,558 B2 * | 11/2008 | Pratt | 700/118 |
| 2005/0171456 A1 * | 8/2005 | Hirschman et al. | 600/592 |
| 2005/0182341 A1 * | 8/2005 | Katayama et al. | 600/587 |

FOREIGN PATENT DOCUMENTS

| | | |
|---|---|---|
| EP | 0663181 | 7/1995 |
| EP | 1454584 | 9/2004 |
| GB | 2186375 A | 8/1987 |
| UA | 54139 C2 | 9/2004 |
| WO | 02059554 | 8/2002 |

\* cited by examiner

SYSTEM AND METHOD FOR VISUALIZING GROUND REACTION FORCES ON A HUMAN BODY

CROSS-REFERENCE TO RELATED APPLICATION

This patent application is a national stage application under 35 U.S.C. 371 of International Application PCT/DE2007/000737, filed on Apr. 25, 2007, which claims priority to German Patent Application No. 10 2006 021788.8, filed on May 9, 2006. The entire content of both are hereby expressly incorporated by reference.

TECHNICAL FIELD

The invention relates to a system and method for detecting and displaying ground reaction forces of a human. The system comprises a measurement plate having at least one sensor device for detecting ground reaction forces, an evaluation device connected to the measurement plate and a projection device. The display system and the method are suitable in particular for measuring the human body and/or prosthetic or orthotic fit components in their relative position to the human body, and for improving the adjustment of a prosthesis set up.

BACKGROUND

In addition to the right selection and adjustment of the prosthesis, the successful provision of a prosthesis for a patient depends to a large extent on the cooperation of the patient and the patient's acceptance of the prosthesis. A technically refined prosthesis does not fulfill its purpose if it is not accepted by the prosthesis wearer, or if it is used incorrectly. Accordingly, it is important for the patient to understand the set up and the function of the prosthesis, and to be aware of the consequences of incorrect handling or setting. Furthermore, prostheses have to be adapted to the individual requirements and circumstances of the prosthesis wearer. To this end, it is important to determine an optimal prosthesis set up for the patient, that is to say the adjustment of the prosthesis components to one another and to the human body, to obtain a sufficiently stable set up and/or high dynamic mobility. An individually adjusted set up of the prosthesis is important, particularly in the case of knee prostheses.

In the display system disclosed in EP 0 663 181 A2, a prosthesis wearer stands on a measurement plate equipped with pressure sensors. The center of gravity of the body of the prosthesis wearer is determined by means of the pressure sensors. The body-gravity line is projected onto the human body using a laser projection unit which generates a vertical, linear light beam. The position of the body-gravity line is adjusted by moving the laser projection unit along a linear guide.

Using this system, the center-of-gravity line of the body can be determined very well with respect to the positions of the joints. Likewise, the measurement data can be conversely determined by particular joints being approached by the projection line so that an appropriate measure can be determined from the traversed path of the laser projection unit.

The prosthesis set up is adjusted by a prosthesist on the basis of the determined body-gravity line and requires some experience. Occasionally the patient does not know why a particular setting is chosen. This can lead to problems with the acceptance.

SUMMARY

It is an object of the present invention to provide an improved system and a method for detecting and displaying ground reaction forces by means of which it is possible to improve the acceptance and adjustment of the prosthesis set up.

The system according to one embodiment of the present invention comprises a measurement plate having at least one sensor device for recording ground reaction forces, an evaluation unit connected to the measurement plate, which evaluates sensor data determined by the sensor device, and a projection device, which projects a strip of light onto the human body based on the evaluated data. In one embodiment, the sensor device is a multi-component force sensor which detects the vertical and horizontal components of the ground reaction force, and the projection device is designed to display the location and orientation of the ground reaction force. The system according to this embodiment is able to detect horizontal forces which occur due to the prosthesis set up, or which occur in static force or dynamic force measurements. The display system may also display the force vector which is acting on the prosthesis or the stump of the prosthesis wearer, and a force profile may be displayed directly on the patient. As a result of this, the effects of a changed prosthesis set up on the direction of the force and thus also on the load on the stump can be clarified for the patient in a direct manner. The adjustment of the prosthesis set up can thus be carried out with an improved acceptance by the prosthesis user. Likewise, it is easier for the prosthesist to adjust the prosthesis set up than before because the changes are immediately visualized on the patient.

In a development of the invention, the projection device is a video projector or data projector, or "beamer." Based on the data evaluated by the evaluation unit, the projection device generates a bar of light which can be rotated or tilted according to the orientation of the ground reaction force vector. For this purpose, it is only necessary to generate a video image in the form of a strip of light on the basis of the evaluated sensor data. This requires little technical complexity. As an alternative to this, a laser projection may be modified so that it can be tilted by using a motor, in particular a stepper motor, so that the orientation of the ground reaction force vector can be imaged on the patient. Whereas the data projector can vary the orientation and width of the bar of light in a simple manner, a laser projection unit in general produces a more focused, contoured photo. The data projector or beamer may be advantageous in that it is possible to superpose additional information, which can be generated by the evaluation unit using stored calculation prescriptions, for example the magnitude of the force in newton or details relating to the prosthesis correction.

In another development of the invention, the system includes a video camera associated with the measurement plate so that the position or movement of the patient can be recorded at the same time as the force measurement using the multi-component force sensors. Combined use of the projection device and the video camera allows for a dynamic observation of the force profile in addition to static observations. The video recording also permits later detailed evaluation of the force profile so that the prosthesis set up can be optimally adjusted by various movement phases or positions.

To avoid parallax errors, which occur particularly in the case of small distances between the projection device and the patient, the system may be used in a sufficiently large space or may be utilized in a tight adjacent arrangement of the combination of projection device and video camera. For example, the video camera and projection device may be arranged on a common optical plane or a common optical axis, preferably at a substantially identical distance from the patient.

The method according to one embodiment of the invention for displaying ground reaction forces, in particular for adjusting a prosthesis set up, measures the ground reaction forces of a patient standing on a measurement plate in both the horizontal and the vertical directions by means of the measurement plate. The point of contact and orientation of the force vector of the ground reaction forces are determined and projected onto the human body so that the ground reaction force, the location and the direction can be visualized on the patient. The prosthesis may then be adjusted accordingly.

In one embodiment, the magnitude of the force can be displayed using a length modulation of the bar of light which represents the ground reaction force vector. Correspondingly, it is longer in the case of larger forces than in the case of smaller forces. The ground reaction force vector projected onto the human body during the measurement of the ground reaction forces may be recorded by a video camera for dynamic observations, in particular for repeated dynamic observations. Hence, it is possible to repeatedly analyze a dynamic display of the profile of the ground reaction force vector. If a data projector is used, it is possible to display both the video images and the force vector projection by means of the data projector so that it is not necessary for a separate screen to be present.

In another development of the invention, the force vector may be displayed in color and/or modulated if particular reference values are exceeded or undershot, for example. Provision can also be made for a geometric modulation. A change in color or magnitude depending on the load can directly supply the prosthesis user or the prosthesist with information regarding a favorable or unfavorable prosthesis set up.

BRIEF DESCRIPTION OF THE DRAWINGS

In the following text, exemplary embodiments of the invention will be explained in more detail on the basis of the attached Figures, in which.

DETAILED DESCRIPTION

Figure 1:
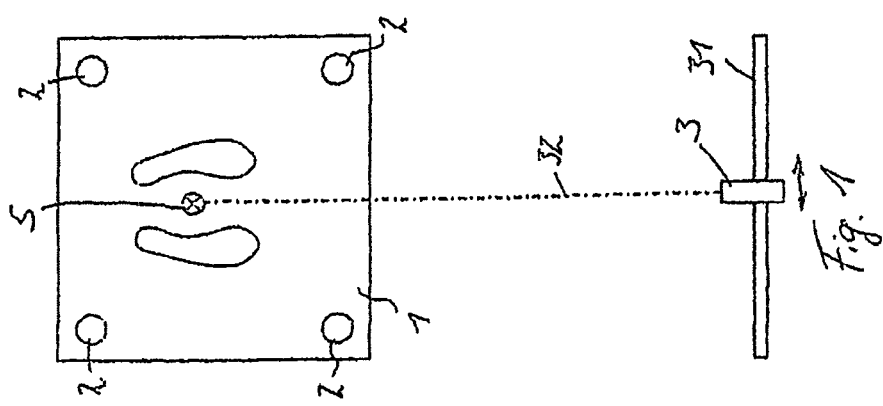
FIG. 1 shows a schematic plan view of a display system in a first embodiment.

FIG. 1 shows a plan view of a display system for displaying reaction forces comprising a measurement plate 1 which stands on the ground via force sensors 2, which in the present case are arranged on the four corners of the measurement plate 1. The foot positions of a human is shown standing on the measurement plate 1.

A projection device 3 is arranged opposite to the measurement plate 1 and in the present case is in the form of a laser projection device. The laser projection device 3 is moveably arranged on a movement device 31. The movement directions are indicated by the double-headed arrow. The force sensors 2 are coupled to an evaluation unit (not illustrated) by means of which the position of the center of gravity of the body 5 of the person standing on the measurement plate 1 is determined on the measurement plate 1. The evaluation unit calculates the movement path of the laser projection device 3 and aligns it so that the laser beam 32, in the form of a bar of light, is projected onto the body of the person located on the measurement plate 1. In the present example, the person is standing on the measurement plate 1 with both feet so that in essence only vertically acting ground reaction forces are recorded by the force sensors 2. Accordingly, the laser beam 32 and the projected bar of light are substantially aligned vertically.

However, should horizontal forces be measured, the display system according to the invention provides for the projection device 3 to be pivoted in such a way that the orientation is shown in addition to the location of the point of contact of the ground reaction force. For this purpose, the laser beam 32 or the projection device 3 can be turned or tilted about an axis parallel to the illustrated laser beam 32.

Figure 2:
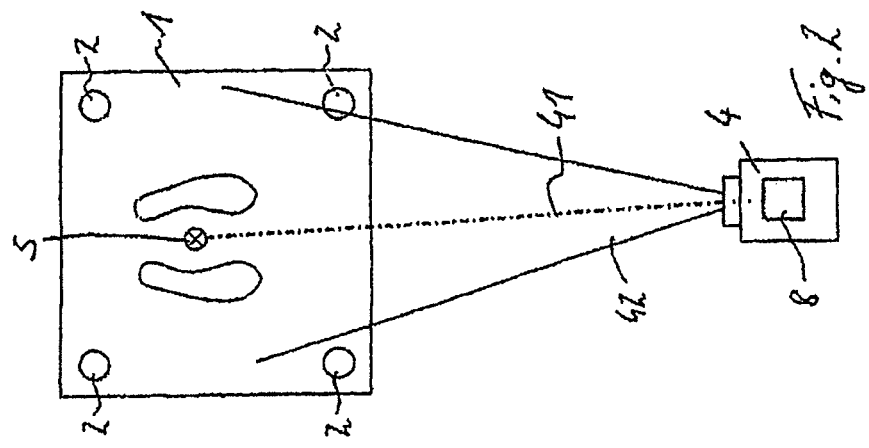
FIG. 2 shows a schematic illustration of a display system in a second embodiment.

An alternative embodiment of the display system is illustrated in FIG. 2, where in place of a moveably mounted laser projector 3, a data projector 4 projects a light beam 41 within the emission region 42 of the data projector 4 (also referred to as a beamer) onto the human located on the measurement plate 1. A substantially vertical orientation of the bar of light 41 is expected in the case of a standing person, as is the case in FIG. 1. This bar of light 41 is arranged on the center of gravity of the body 5. A video camera 8, which can record the projection of the bar of light 41 during the measurement of the ground reaction force, is installed above the data projector 4, preferably on the latter's optical axis. As long as the video camera 8 lies on one optical plane with the data projector 4, preferably one above the other and with the same optical effective distance, there is no parallax error so that the display is sufficiently accurate.

Figure 3:
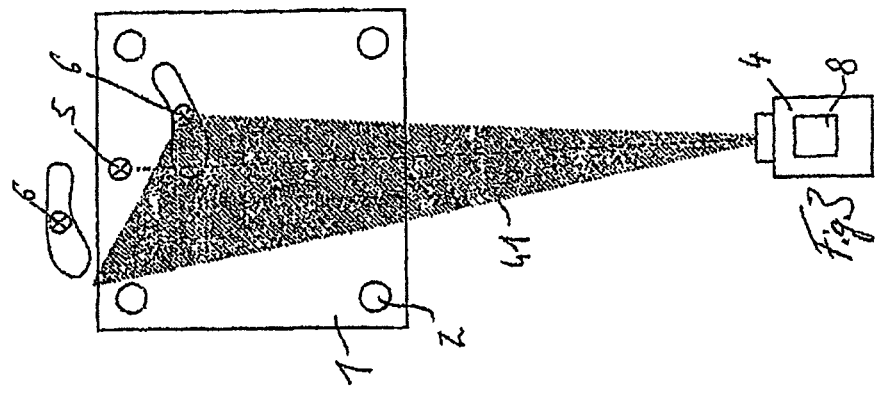
FIG. 3 shows an application of the system in accordance with FIG. 2.

FIG. 3 illustrates the display system in accordance with FIG. 2, in which the person stands on the measurement plate 1 with only one foot. The force induction points 6 through the feet, possibly prosthesis feet, are thus located for one on the measurement plate 1 and for the other next to it. Due to a possibly acting horizontal force, the beam of light 41 projected from the data projector 4 to the center of gravity of the body 5 is no longer vertical but is tilted, starting from the force induction point 6 on the measurement plate 1 and corresponding to the orientation of the ground reaction force vector, so that the orientation of the ground reaction force vector is displayed and projected onto the body. This projection can be recorded by the video camera 8. By these means it is possible to record a walking human with one foot treading on the measurement plate 1 and the other one treading next to it. During the progression of the step or the steps, the ground reaction forces can then be projected onto the human body and dynamically observed repeatedly and in detail using the video image. The video image recorded by the video camera 8 can be played back by the bearer 4, possibly onto a screen or a wall located behind the measurement plate 1.

Figure 4:
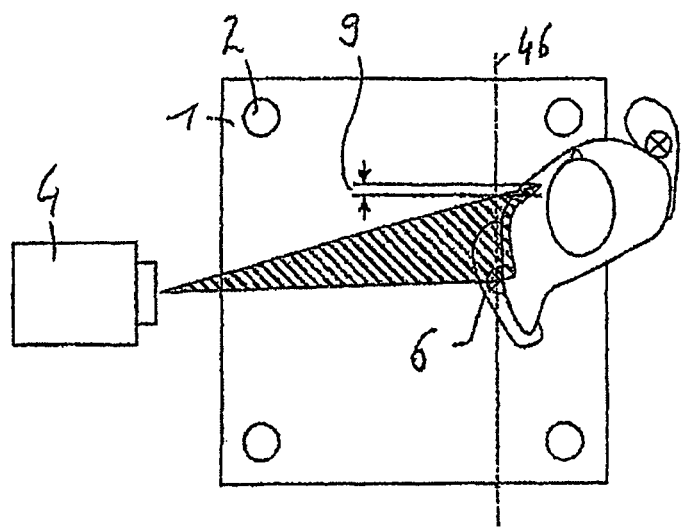
FIG. 4 shows an alternative illustration of FIG. 3.

FIG. 4 illustrates the display system according to FIG. 3, in which the light beam 41, which represents the ground reaction force vector, is projected onto a person. The projection can be geometrically modulated or modulated in color in order to indicate the magnitude of the ground reaction force vector, or whether the ground reaction forces are within an acceptable or prescribed range. Using this, it is possible to determine whether a prosthesis has been adjusted correctly, that is to say whether an expedient prosthesis set up is present. Furthermore, it is possible to undertake changes on the prosthesis while the ground reaction force vector is being projected on the person standing on the measurement plate 1. During the change in the prosthesis set up, the bar of light 41 or laser beam is then tilted by a measure relating to the change in ground reaction force. In order to avoid parallax errors to the greatest possible extent, the view of the prosthesis is advantageously from the direction of the projector 4.

FIG. 4 illustrates a projection error 9 which is caused due to the uneven projection surface on the human body; the numerically determined and optically correct projection surface 46 lies in the plane perpendicular to the measurement plate 1 and passes through the force induction point 6. This projection error 9 is generally small and can be neglected. The length modulation can be calculated using the intercept theorem and knowledge of the force induction points 6 due to the various force sensors 2 and their evaluation.

Figure 5:
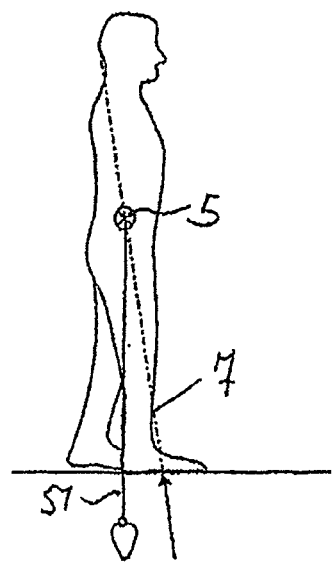
FIG. 5 shows a schematic illustration of a projection of a ground reaction force.

FIG. 5 shows a side view of a patient with the center of gravity of the body 5, the body-gravity line 51 being perpendicular and the ground reaction force 7 which is aligned at an angle to the horizontal. The bar of light is projected along the orientation of the ground reaction force 7.

Figure 6:
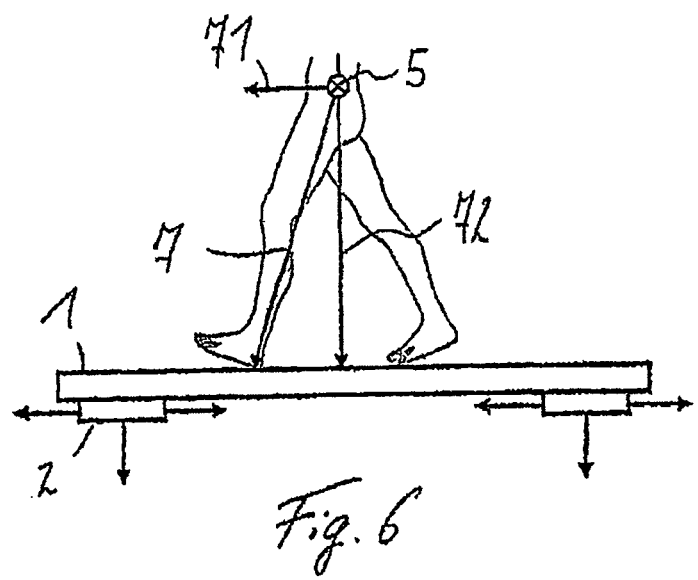
FIG. 6 shows a first embodiment of a measurement plate.
Figure 7:
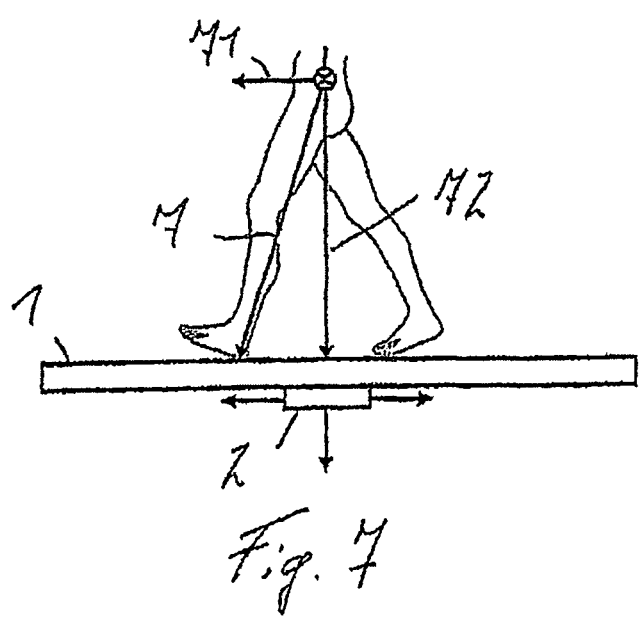
FIG. 7 shows a variation of FIG. 6.

FIGS. 6 and 7 show different designs of the measurement plate 1 and the composition of the ground reaction force 7 from a vertical component 72 and a horizontal component 71 which contact at the center of gravity of the body 5. The ground reaction force 7 is calculated and the orientation of the vertical component 72 and horizontal component 71 is measured using the force sensors 2 which are multi-component force sensors. In accordance with FIG. 6, a plurality of force sensors 2 are arranged at the corners of the measurement plate 1 and in accordance with FIG. 7, one multi-component measurement sensor 2 is arranged centrally on the measurement plate 1. All force sensors 2 determine the vertical and horizontal forces during the static or dynamic load. As a result, it is possible to observe the static and dynamic force profile acting on the patient and the prosthesis while standing or walking. When using a data projector 4, it is possible to superpose additional information such as the magnitude of the respective components or adjustment suggestions in addition to the bar of light or the laser beam.

The invention claimed is:

1. A method for displaying ground reaction forces for adjusting a prosthesis set up on a human, the method comprising:
    positioning a human on a measurement plate comprising at least one multi-component force sensor;
    measuring the vertical and horizontal components of a ground reaction force of the human positioned with only one leg supported on the measurement plate and another leg supported on a ground surface adjacent to the measurement plate;
    determining a force vector of the ground reaction force using the measured vertical and horizontal components of the ground reaction force;
    projecting and displaying a point of contact and an orientation of the force vector of the ground reaction force on the human positioned on the measurement plate, wherein the force vector is projected onto the human by a data projector or a moveable laser projection unit.

2. The method of claim 1, wherein a magnitude of the ground reaction force is projected and displayed by modulating a length of the projection.

3. The method of claim 1, wherein the display of the vector of the ground reaction force on the human is recorded by a video camera during the measurement of the ground reaction force and is displayed in a video image display.

4. The method of claim 1, wherein a profile of the ground reaction force vector is displayed dynamically.

5. The method of claim 1, wherein the projection of the ground reaction force vector is modulated in color or geometrically depending on the orientation and/or magnitude of the ground reaction force vector.

6. A method for displaying ground reaction forces of a human, the method comprising:
    positioning a human on a measurement plate comprising at least one multi-component force sensor;
    measuring the vertical and horizontal components of a ground reaction force of the human positioned with only one leg supported on the measurement plate and another leg supported on a ground surface adjacent to the measurement plate;
    determining a force vector of the ground reaction force using the measured vertical and horizontal components of the ground reaction force;
    projecting and displaying a magnitude and direction of the force vector of the ground reaction force on the human positioned on the measurement plate.

7. The method of claim 6, wherein the magnitude of the force vector of the ground reaction force is projected and displayed by modulating a length of the projection.

* * * * *